(12) United States Patent
Kim et al.

(10) Patent No.: US 10,131,891 B2
(45) Date of Patent: Nov. 20, 2018

(54) METHOD OF USING INSULIN FOR CONTROLLING GLYCOSYLATION OF RECOMBINANT GLYCOPROTEIN

(71) Applicant: LG CHEM, LTD., Seoul (KR)

(72) Inventors: Kyu Yong Kim, Daejeon (KR); Soo Hyun Ryu, Daejeon (KR); Sam Sook Seol, Daejeon (KR); Sun Young Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/541,123

(22) PCT Filed: Dec. 30, 2015

(86) PCT No.: PCT/KR2015/014512
§ 371 (c)(1),
(2) Date: Jun. 30, 2017

(87) PCT Pub. No.: WO2016/108638
PCT Pub. Date: Jul. 7, 2016

(65) Prior Publication Data
US 2017/0342392 A1 Nov. 30, 2017

(30) Foreign Application Priority Data
Dec. 31, 2014 (KR) .................. 10-2014-0195976

(51) Int. Cl.
| | | |
|---|---|---|
| *C12N 9/24* | (2006.01) | |
| *C07K 14/705* | (2006.01) | |
| *C07K 16/00* | (2006.01) | |
| *C07K 19/00* | (2006.01) | |
| *C12P 19/18* | (2006.01) | |
| *C12P 21/00* | (2006.01) | |
| *A61K 38/17* | (2006.01) | |
| *C07K 14/62* | (2006.01) | |
| *C12N 15/52* | (2006.01) | |
| *C12N 15/74* | (2006.01) | |

(52) U.S. Cl.
CPC ............ *C12N 9/24* (2013.01); *A61K 38/1741* (2013.01); *C07K 14/62* (2013.01); *C07K 14/705* (2013.01); *C07K 16/00* (2013.01); *C07K 19/00* (2013.01); *C12N 15/52* (2013.01); *C12N 15/74* (2013.01); *C12P 19/18* (2013.01); *C12P 21/00* (2013.01); *C07K 2317/14* (2013.01); *C07K 2317/21* (2013.01); *C07K 2317/41* (2013.01)

(58) Field of Classification Search
CPC .......... C12N 9/24; C12N 15/52; C12N 15/62; C12N 15/74; A61K 38/1741; C07K 2317/14; C07K 2317/21; C07K 2317/41
See application file for complete search history.

(56) References Cited

U.S. PATENT DOCUMENTS

| | | | |
|---|---|---|---|
| 7,317,095 B2 | 1/2008 | Brondyk et al. | |
| 8,129,145 B2 * | 3/2012 | Lasko ................... | C07K 16/18 435/404 |
| 8,617,878 B2 | 12/2013 | Crowell et al. | |
| 9,944,968 B2 * | 4/2018 | Yang ................... | C12N 5/0018 |
| 2012/0276631 A1 | 11/2012 | Bengea et al. | |
| 2015/0307888 A1 | 10/2015 | Malphettes et al. | |

FOREIGN PATENT DOCUMENTS

| | | |
|---|---|---|
| JP | H0947284 A | 2/1997 |
| JP | 2005520573 A | 7/2005 |
| JP | 2010246541 A | 11/2010 |
| JP | 2012502630 A | 2/2012 |
| KR | 10-2009-0029841 A | 3/2009 |
| KR | 10-2011-0139292 A | 12/2011 |
| KR | 10-2012-0059222 A | 6/2012 |
| KR | 10-2012-0134116 A | 12/2012 |
| RU | 2463345 C2 | 10/2012 |
| WO | 9639488 A1 | 12/1996 |
| WO | 99/61650 A1 | 12/1999 |
| WO | 2007034809 A1 | 3/2007 |
| WO | 2011099028 A1 | 8/2011 |
| WO | 2013006479 A2 | 1/2013 |
| WO | 2015/026846 A1 | 2/2015 |

OTHER PUBLICATIONS

Lee J-H, et al. (2013). Biologicals. 41:77-83. (http://dx.doi.org/10.1016/j.biologicals.2012.09.001).*
Gawlitzek M, et al. (2000). Biotechnology and Bioengineering. 68:637-646.*
Sigma Aldrich website (Feb. 22, 2018) for product #c8862. https://www.sigmaaldrich.com/catalog/product/sigma/c8862?lang=en&region=US.*
Biol-N'garagba, Marie-Claire et al., "Regulation of the intestinal glycoprotein glycosylation during postnatal development: role of hormonal and nutritional factors", Biochimie, 2003, vol. 85, pp. 331-352.
Kwon, Oh-Seok et al, "Guideline on Characterization and Specification of Glycan Structure in Glycoprotein Products", =FDC Legislation Research V, vol. 1, 2, 13-21, 2010.
Search Report and Written Opinion issued for International Application No. PCT/KR2015/014512 dated Apr. 28, 2016, 8 pages.
Office Action issued for New Zealand patent application No. 733430 dated Dec. 18, 2017, 5 pages.
EPO Communication cited in 15875732.8 dated Jun. 25, 2018, 6 pages.
First Office Action cited in Japanese application No. 2017-535399, dated May 28, 2018, 7 pages.
First Office Action cited Russian application No. 2017124160, dated May 18, 2018, 6 pages.

* cited by examiner

*Primary Examiner* — Robert S Landsman
(74) *Attorney, Agent, or Firm* — Rothwell, Figg, Ernst & Manbeck, P.C.

(57) ABSTRACT

The present invention relates to a method for controlling a glycosylation pattern of a recombinant glycoprotein, comprising culturing a cell comprising polynucleotide encoding a recombinant glycoprotein in a culture medium comprising insulin.

15 Claims, 2 Drawing Sheets

[Fig.1]
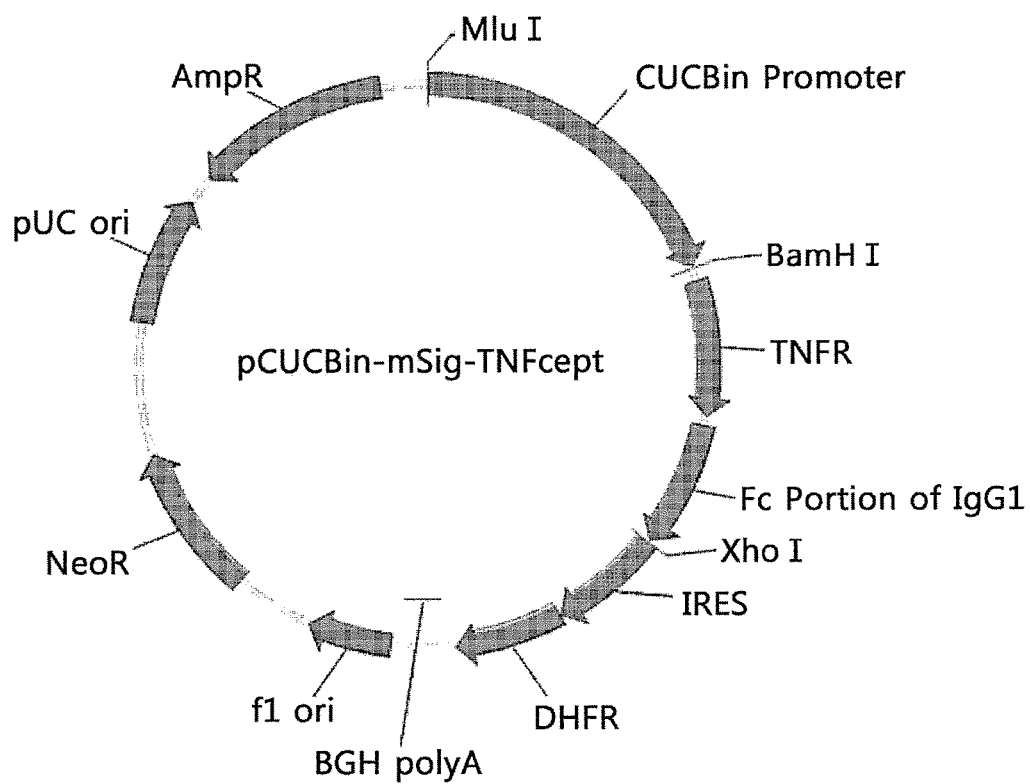

[Fig. 2]
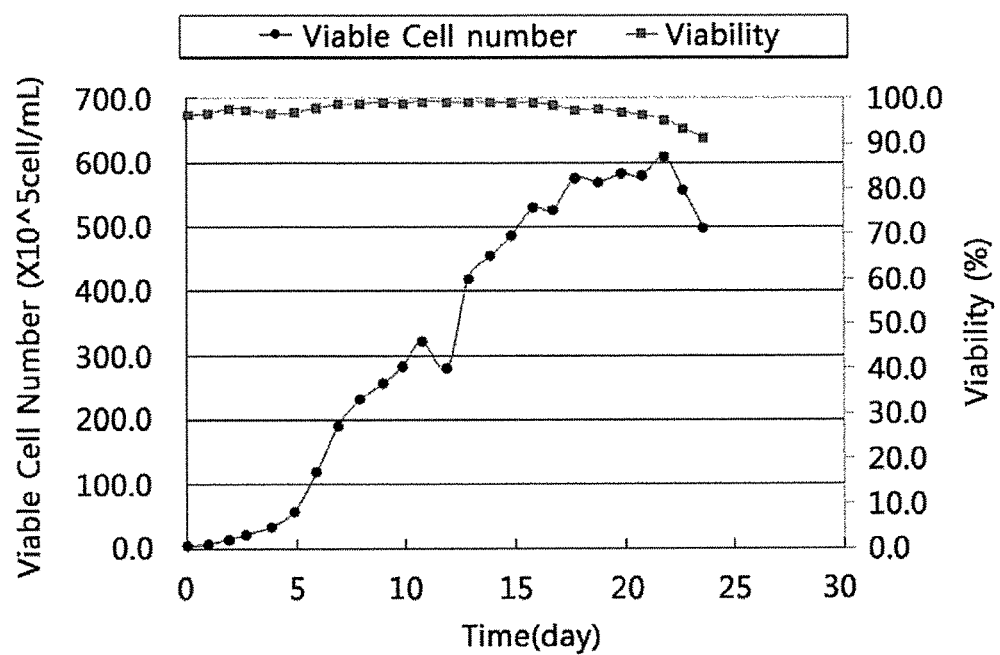

METHOD OF USING INSULIN FOR CONTROLLING GLYCOSYLATION OF RECOMBINANT GLYCOPROTEIN

CROSS-REFERENCE TO RELATED APPLICATIONS

This application is a 35 U.S.C. § 371 National Phase Entry Application from PCT/KR2015/014512, filed on Dec. 30, 2015, and designating the United States, which claims priority under 35 U.S.C. § 119 to Korean Patent Application No. 10-2014-0195976, filed on Dec. 31, 2014, the entire disclosures of which are incorporated herein by reference.

TECHNICAL FIELD

The present invention relates to a method for controlling glycosylation of a recombinant glycoprotein.

BACKGROUND ART

As a TNFR-Fc fusion protein in which a ligand binding part of a human p75 TNF-α receptor (TNFR, TNF-α receptor) is linked to an Fc fragment of human $IgG_1$, Etanercept was released by Amgen under the trade name of Enbrel in 2002. Etanercept competitively inhibits in vivo binding between TNF-α receptors on the surface of a cell, thereby inhibiting a TNF-α-related immune response. Accordingly, as a TNF-α inhibitor, Etanercept is used for rheumatoid arthritis, psoriasis, ankylosing spondylitis, etc., and clinical studies for its application to vasculitis, Alzheimer's disease, and Crohn's disease are in progress.

Meanwhile, a gene recombinant pharmaceutical product is a pharmaceutical product containing a peptide, a protein, etc., produced by using a genetic manipulation technique as an active ingredient. Use of biotechnology is advantageous in that it is possible to obtain a large number of highly pure recombinant proteins which are difficult to obtain in a natural state, but an expression structure itself may be unstable since a gene of a target protein is inserted into a host cell from outside. Besides, proteins are produced by expressing the gene in a microorganism or a cell of an animal or plant, but not in the human body, the recombinant proteins may be different from native proteins in terms of structural, physicochemical, immunochemical, and biological properties or features (Kwon, et al., FDC Legislation Research V, vol. 1, 2, 13-21, 2010).

In particular, in the case of a glycoprotein, glycosylation and a structure or form of a glycoform (sugar chain) may differ according to a culture condition. In other words, in the process of glycoprotein production, difference in glycoform structures or the amounts of saccharides constituting the glycoform structure lead to various types of glycoforms, thereby causing heterogeneity according to differences in production conditions. In the case of glycoproteins with different glycoform structures, they are different from native forms in terms of in vivo movement or tissue distribution, or are antagonistic to the native forms, causing an adverse reaction. When administered continuously for a long period of time, they act as antigens and may cause an immunological problem.

As described above, as the glycoforms may become an important factor that may affect a pharmaceutical effect and in vivo movement, controlling the glycoprotein structures is very important in the field of development of recombinant glycoprotein products for medicines and development of mass production technology.

In this regard, Korean Patent Publication No. 2011-0139292, as a prior art, discloses control of protein glycosylation and compositions and methods related thereto, and Korean Patent Publication No. 2012-0134116 discloses a method for increasing N-glycosylation site occupancy on therapeutic glycoproteins.

DISCLOSURE OF INVENTION

Technical Problem

With the above background, the present inventors have made extensive efforts to find a method for controlling glycosylation of a recombinant glycoprotein, and as a result, have confirmed that the glycosylation of the recombinant glycoprotein can be controlled when a culture medium containing insulin is used, thereby completing the present invention.

Technical Solution

A main object of the present invention is to provide a method for controlling a glycosylation pattern of a recombinant glycoprotein, comprising culturing a microorganism comprising a polynucleotide encoding the recombinant glycoprotein in a culture medium comprising insulin.

Another object of the present invention is to provide a method for controlling a glycosylation pattern of a recombinant glycoprotein, comprising (a) culturing a microorganism comprising a polynucleotide encoding a recombinant glycoprotein in a culture medium to grow the microorganism; and (b) adding insulin in the culture medium and culturing the same to produce a glycoprotein.

Advantageous Effect

The method for controlling the glycosylation of the recombinant glycoprotein according to the present invention can control an activity, folding, secretion, stability, a half-life in plasma, and an immune response of the recombinant glycoprotein.

DESCRIPTION OF DRAWINGS

FIG. 1 shows a cleavage map of pCUCBin-mSig-TNFcept.

FIG. 2 shows the number of viable cells (unit: $10^5$ cells/mL) and viability (%) according to cell culture time (unit: day) in an exemplary embodiment of the present invention.

BEST MODE

As an aspect to achieve the above objects, the present invention provides a method for controlling a glycosylation pattern of a recombinant glycoprotein, comprising culturing a microorganism comprising a polynucleotide encoding the recombinant glycoprotein in a culture medium comprising insulin.

The glycoprotein refers to a protein in which a saccharide binds to a specific amino acid of a polypeptide, and the saccharide may refer to a glycoform, e.g., one in which at least one or two monosaccharides are linked. As an example, the glycoform, as an oligosaccharide in which various monosaccharides are linked to a glycoprotein, may include a monosaccharide such as fucose, N-acetylglucosamine, N-acetylgalactosamine, galactose, mannose, sialic acid, glucose, xyloses, mannose-6-phosphate, etc.; a branched form thereof; etc.

As an example, the recombinant glycoprotein may be an immunoglobulin fusion protein. The immunoglobulin fusion protein may include the Fc region which is a part of the immunoglobulin, including the heavy chain constant domain 2 ($C_H2$), the heavy chain constant domain 3 ($C_H3$), and the hinge region, excluding the variable domains of the heavy and light chains, the heavy chain constant domain 1 ($C_H1$), and the light chain constant domain ($C_L1$) of the immunoglobulin (Ig).

As another example, the recombinant glycoprotein may be a TNFR-Fc fusion protein.

The tumor necrosis factor receptor (TNFR) refers to a receptor protein which binds to a TNF-α. The TNFR protein may be a TNFRI (p55) or TNFRII (p75) protein, preferably TNFRII protein, but is not limited thereto. Additionally, the TNFRII may be alternatively used with a tumor necrosis factor receptor superfamily member 1B (TNFRSF1B). The TNFRII protein is divided into 4 domains and transmembrane regions, e.g., a TNFRII protein consisting of 235 amino acids including 4 domains and transmembrane, but is not limited thereto. Information regarding the TNFRI and TNFRII proteins can be obtained from known databases such as National Institutes of Health GenBank. For example, the TNFRI and TNFRII proteins may be the proteins of which the accession number is NP_001056 or P20333, but are not limited thereto.

For having an activity of binding to TNF-α, which is known to cause various diseases when overexpressed in vivo, the TNFR protein can be used for treatment of diseases mediated by TNF-α. In order to be used for said purpose, the TNFR protein can be produced and used in a form of a fusion protein with a half-life increased by fusion of the Fc region of an immunoglobulin and the TNFR protein.

The tumor necrosis factor receptor (TNFR)-Fc fusion protein refers to a fusion protein in which all or a portion of the TNFR protein is linked to the Fc region of the immunoglobulin by an enzymatic reaction or a product in which the two polypeptides are expressed in one polypeptide through genetic manipulation. The TNFR-Fc fusion protein may have TNFR protein and the Fc region of the immunoglobulin directly linked via a peptide linker, but is not limited thereto. A non-limiting example of the TNFR-Fc fusion protein may be Etanercept (U.S. Pat. Nos. 7,915,225; 5,605,690; Re. 36,755).

The TNFR-Fc fusion protein may be produced by fusion of all or a portion of a TNFR protein with the Fc region of an immunoglobulin, e.g., 232 amino acids of the Fc region of an immunoglobulin including the hinge region and the $1^{st}$ to $235^{th}$ amino acid sites of the TNFRII, but is not limited thereto. Additionally, the TNFR-Fc fusion protein may be codon-optimized according to a host cell to be expressed and may be, for example, a TNFR-Fc fusion protein codon-optimized specifically to a CHO cell, but is not limited thereto. The TNFR-Fc fusion protein is not only an amino acid sequence, but also an amino acid sequence which is 70% or more, preferably 80% or more, more preferably 90% or more, still more preferably 95% or more, most preferably 98% similar to the amino acid sequence, and includes all proteins which have the activity of substantially binding to TNF-α. It is obvious that as long as the sequence having such similarity is an amino acid sequence identical to TNFR-Fc fusion protein or an amino acid sequence having a corresponding biological activity, a protein mutant having amino acid sequences of which a part is deleted, modified, substituted, or added falls within the scope of the present invention.

The Fc refers to a part of the immunoglobulin, including the heavy chain constant domain 2 ($C_H2$), the heavy chain constant domain 3 ($C_H3$), and the hinge region, excluding the variable domains of the heavy and light chains, the heavy chain constant domain 1 ($C_H1$), and the light chain constant domain ($C_L1$) of the immunoglobulin (Ig). Additionally, the Fc region of the present invention includes not only a native form of an amino acid sequence but also an amino acid sequence derivative thereof. The amino acid sequence derivative means that one or more amino acid residues of a native form of an amino acid sequence have different sequences due to deletion, insertion, conservative or non-conservative substitution, or a combination thereof. Additionally, the immunoglobulin Fc region may be an Fc region derived from IgG, IgM, IgE, IgA, IgD, or a combination or hybrid thereof. Additionally, the immunoglobulin Fc region is preferably derived from an IgG known to improve half-life of a binding protein, and more preferably derived from an IgG1, but is not limited to its subclass and can be obtained from any subclass of IgG (IgG1, IgG2, IgG3, and IgG4).

The Fc region can genetically produce or obtain a gene encoding the Fc region by using a recombinant vector or cutting a purified polyclonal antigen or monoclonal antigen with an appropriate lyase such as papain, pepsin, etc., respectively.

The TNFR-Fc fusion protein can be obtained by introducing an expression vector including a polynucleotide encoding the fusion protein into a host cell and expressing the same. In an exemplary embodiment of the present invention, a pCUCBin-mSig-TNFcept vector was used as the expression vector including a polynucleotide encoding the TNFR-Fc fusion protein and was transduced into a CHO cell to express a TNFR-Fc fusion protein.

In the present invention, the microorganism can be used to have the same meaning as the host cell or transformant. A non-limiting example may be an animal cell line, plant, or yeast host cell. In an exemplary embodiment of the present invention, Chinese Hamster Ovary cell (CHO cell) was used as the microorganism, but is not limited thereto as long as the microorganism can be transformed by a polynucleotide encoding the recombinant glycoprotein.

The polynucleotide, as long as it can be expressed inside the microorganism, can be inserted into a chromosome and located therein or located outside the chromosome. The polynucleotide includes RNA and DNA which encode the target protein. A method for including the polynucleotide is not limited as long as the method is used in the art. As an example, the polynucleotide can be included inside a microorganism in a form of an expression cassette, a gene construct including all essential elements required for self-expression. As another example, a method for modifying by an expression vector including a sequence of the polynucleotide encoding the target protein operably connected to a suitable regulation sequence so that the target protein can be expressed in an appropriate host cell can be used. The regulation sequence includes a promoter initiating transcription, a random operator sequence for regulation of the transcription, a sequence encoding a suitable mRNA ribosome-binding domain, and a sequence for regulation of transcription and translation. The vector, after being transformed into a suitable host cell, may be replicated or function irrespective of the host genome, or may be integrated into the host genome itself. The vector used in the present invention may not be specifically limited as long as the vector is replicable in the host cell, and any vector known in the art may be used.

The glycosylation pattern of the recombinant glycoprotein means an expression pattern of a glycoform, which appears through glycosylation of the glycoprotein. Examples of the glycosylation pattern include presence of glycosylation which connects a saccharide to a protein, type of a saccharide, type of glycosylation, content of saccharide, composition of monosaccharide (saccharides), including molar ratio, location of glycoform, structure of glycoform including sequence, location of glycosylation, glycosylation occupancy, number of glycoforms, and relative contents according to structure. Difference in biological activity or in vivo stability may appear according to the glycosylation pattern of the recombinant glycoprotein.

In the present invention, the insulin may control N-linked glycosylation of the recombinant glycoprotein. In the present invention, the N-linked glycosylation may be used to have the same meaning as N-glycosylation. As an example, the insulin may reduce the content of N-glycan of the recombinant glycoprotein. In the present invention, the N-glycan may be used to have the same meaning as N-glycoform, and may refer to a case in which a saccharide is connected to asparagine of protein.

In the present invention, the insulin may control O-linked glycosylation of the recombinant glycoprotein. In the present invention, the N-linked glycosylation may be used to have the same meaning as O-glycosylation. As another example, the insulin may reduce the content of O-glycan of the recombinant glycoprotein. In the present invention, the O-glycan may be used to have the same meaning as O-glycoform, and may refer to a case in which a saccharide is connected to serine or threonine of protein.

In the present invention, the insulin may control the N-linked glycosylation and O-linked glycosylation of the recombinant glycoprotein.

In an exemplary embodiment of the present invention, the insulin addition appeared to influence the glycosylation pattern of the glycoprotein (Table 2). Specifically, it was confirmed that the N-glycan and/or O-glycan content is controlled to be reduced by addition of the insulin. In particular, among culturing processes of a cell capable of producing glycoprotein, addition of insulin during the production phase was confirmed to play an important role in control of the glycosylation pattern.

The insulin concentration may be 0.0001 mg/L to 1 g/L relative to the total volume of the culture medium. In an exemplary embodiment of the present invention, it was confirmed that as the insulin concentration increases, the N-glycan and/or O-glycan content could be controlled to be reduced (Table 2).

The culture medium is not limited as long as it is used for culturing a microorganism or host cell including a polynucleotide encoding a glycoprotein in the art. For example, the culture medium may include an amino acid such as L-glutamine, thymidine, alanine, arginine monohydrochloride, asparagine monohydrate, aspartic acid, cysteine, glycine, histidine, isoleucine, leucine, lysine monohydrochloride, methionine, phenylalanine, proline, serine, threonine, tryptophan, tyrosine, (disodium salt, dehydrate), and valine. As another example, the culture medium may include glucose, sodium bicarbonate, sodium chloride, calcium chloride anhydrous, cupric sulfate pentahydrate, ferric nitrate nonahydrate, ferrous sulfate heptahydrate, potassium chloride, magnesium sulfate anhydrous, magnesium chloride anhydrous, sodium phosphate (monobasic or dibasic, monohydrate), zinc sulfate heptahydrate, hypoxanthine, putrescine dihydrochloride, sodium pyruvate, biotin, D-calcium pantothenate, choline chloride, cyanocobalamin, folic acid, i-inositol, nicotinamide, pyridoxal monohydrochloride, pyridoxine monohydrochloride, riboflavin, thiamine monohydrochloride, glucose anhydrous, potassium chloride, sodium phosphate ($NaH_2PO_4 \cdot H_2O$), sodium hydrogen carbonate ($NaHCO_3$), HEPES (free acid), dextran sulfate, sodium chloride, ascorbic acid, D-biotin, Hypep 1510, or a combination of two or more. For initial seed culture, MTX may be further included for an increase in expression level.

The culturing may be a perfusion culturing method. The culturing may be a culturing method of perfusing culture fluid around a microorganism. Through the perfusion culturing method, the insulin concentration can be easily controlled according to a target glycosylation pattern.

As another aspect, the present invention provides a method for controlling a glycosylation pattern of a recombinant glycoprotein, comprising (a) culturing a microorganism comprising a polynucleotide encoding a recombinant glycoprotein in a culture medium to grow the microorganism; and (b) adding insulin in the culture medium and culturing the same to produce a glycoprotein.

As an example, the recombinant glycoprotein may be an immunoglobulin fusion protein. As another example, the recombinant glycoprotein may be TNFR-Fc fusion protein, which is described above.

Step (a), which is a growth phase, may further include seed culturing.

The culture medium of step (a) may not include insulin.

Step (b) may be a step of adding insulin at different concentrations according to a target glycosylation pattern. In an exemplary embodiment of the present invention, it appeared in the growth phase that the N-glycan and/or O-glycan contents vary according to addition of insulin. Specifically, it was confirmed that the insulin addition can control N-glycan and/or O-glycan contents to be reduced. In particular, among culturing processes of a cell capable of producing glycoprotein, addition of insulin during a production phase was confirmed to play an important role in control of a glycosylation pattern.

The insulin concentration may be 0.0001 mg/L to 1 g/L relative to the total volume of the culture medium. It was confirmed that as the insulin concentration increases, the N-glycan and/or O-glycan content could be controlled to be reduced (Table 2).

The insulin may control N-linked glycosylation and O-linked glycosylation of a recombinant glycoprotein. As an example, the insulin may reduce the N-glycan content of the recombinant glycoprotein. As another example, the insulin may reduce the O-glycan content of the recombinant glycoprotein.

As another aspect, the present invention provides a culture medium composition for controlling the recombinant glycoprotein glycosylation pattern. The insulin may be included in a concentration of 0.0001 mg/L to 1 g/L relative to the total volume of the culture medium.

For example, the culture medium may be used only during the production phase among microorganism culturing processes.

MODE FOR INVENTION

Hereinbelow, the present invention will be described in detail with accompanying exemplary embodiments. However, the exemplary embodiments disclosed herein are only for illustrative purposes and should not be construed as limiting the scope of the present invention.

Example 1: Preparing Cell Line for Glycoprotein Production 1-1. Preparing Vector Methods commonly used in molecular biology such as treatment of restriction enzyme, purification of plasmid DNA, conjugation of DNA sections, and transformation of *E. coli* were conducted by applying minimum modifications to the methods introduced in Molecular Cloning ($2^{nd}$ edition) of Sambrook, et al.

A human p75 TNF receptor (TNFR) gene was cloned using a cDNA library which uses mRNA isolated from a HUVEC cell line as a template, and the cloned gene was fused with the Fc region of a human $IgG_1$ to obtain a TNFR-$IgG_1$. A pCUCBin-mSig-TNFcept vector was prepared using a pTOP-BA-RL-pA vector (Korean Patent Publication No. 10-2012-0059222; comprising "CMVe", "CB", and "beta-actin intron") as a template and the TNFR-$IgG_1$.

1-2. Culturing Mother Cell

CHO/dhfr− (CHO DXB11) was used as a mother cell. CHO/dhfr− is a cell isolated from CHO cell and is deficient in dihydrofolate reductase (DHFR).

1-3. Transformant and Selecting Cell Line for Production

A transformant cell was prepared using CHO/dhfr− (CHO DXB11) and the pCUCBin-mSig-TNFcept vector including p75 TNF receptor (TNFR) gene, and the gene was amplified using MTX concentration. The cells identified as the transformant cells and monoclines were chosen as the cell line for production. The cell lines were then inserted into a glass jar and stored in liquid nitrogen.

Example 2: Culturing Cell Line for Glycoprotein Production and Harvesting Protein Different culture media were used according to culturing phase. Insulin was added to 5.8 g/L of media X011SB (Merck Millipore, Cat. No. 102443) to prepare the basic culture medium. The culture medium (Media EC-SI) in which 10 g/L of glucose anhydrous (Sigma) and 0.584 g/L of glutamine, glycine, and serine (Sigma) were added to the basic culture medium was used for the seed cultivation phase. The culture medium (EC-GM) in which 5 g/l of glucose anhydrous and 0.584 g/L of L-glutamine, glycine, and serine were added to the basic culture medium for the growth phase. The culture medium (EC-PM) in which 15 g/L of glucose anhydrous and 0.584 g/L of L-glutamine, glycine, and serine were added to the basic culture medium was used for the production phase.

The glass jar containing the cell strain prepared in Example 1 was quickly defrosted in a water tank, and the cells therein were moved to a falcon tube containing 10 mL of the culture medium. The resulting cells were centrifuged, and the first supernatant was removed. The cells were then resuspended with 10 mL of Media EC-SI and were inoculated into an Erlenmeyer flask to a final volume of 50 mL. Using a 5 L CelliGen310 cell culture bioreactor, the cells were cultured to obtain 2 L based on working volume. When the viable cell number reached $2 \times 10^6$ cells/mL through five times of seed culturing, the culture medium started to change to EC-GM through the perfusion culturing. As the viable cell number increased, the exchange rate of the culture medium increased to differentiate the cells effectively. When the viable cell number reached $1.5 \times 10^7$ cells/mL (FIG. 2), the culture medium changed to EC-PM, proceeding from the growth phase to the production phase. The harvest was conducted a total of four times, and the harvested protein was purified. The resulting value was the average value of the four harvests.

Example 3: Analyzing Glycan Content 3-1. Analyzing O-Glycan Content

The specimen purified in Example 2 was diluted with 25 mM of sodium phosphate buffer at pH 6.3 to be 100 μL at a concentration of 1.0 mg/mL. 4 μL of N-glycosidase F (1 U/μL, Roche), 2 μL of neuraminidase (1 U/100 μL), and 2 μL of trypsin (1 mg/mL, Promega) were added to each specimen and reacted at 37° C. for 18 hours. LC-MS analysis was then conducted.

80 μL of the specimen was inoculated, and then tryptic peptide was analyzed using C18 RP (4.6 mm×250 mm, 5 μm, 300 Å; Vydac, Cat. No. 218TP54). Mobile phase A used 0.1% TFA in water, and mobile phase B used 0.1% TFA in 80% cold CAN. The analysis was conducted in a gradient condition for 150 minutes. Using a UV detector, a peptide was detected at 215 nm, and the subject separated through LC was connected to a mass spectrometer (LTQ XL, Thermo) for MS analysis to calculate a relative area (%) of 0-glycopeptide.

3-2. Analyzing N-Glycan Content

The specimen purified in Example 2 and a reference standard (Etanercept, Pfizer) were diluted with the specimen diluent (25 mM sodium phosphate (pH 6.3 buffer)) to be 3.0 mg/mL. 100 μL of each specimen and 6 μL of N-glycosidase F solution were mixed and reacted at 37° C. for 20 hours. 400 μL of ethanol was added to the solution after the reaction and was mixed in a vortex. The resulting solution was centrifuged, and the supernatant was then transferred to an Eppendorf tube and dried completely using a speed-vac concentrator. After adding 10 μL of a 2-AA labeling agent to the dried specimen and mixing them, the mixture was reacted at 45° C. and cooled at room temperature.

A GlycoClean S cartridge was put on a disposable culture tube, and then distilled water, 30% acetate, and acetonitrile were perfused sequentially. The cooled specimen was loaded onto the center of the cartridge membrane and perfused with acetonitrile. In order to elute N-glycan, distilled water was added to the cartridge for collection in the Eppendorf tube. The resulting glycan solution was lyophilized and stored until it was analyzed.

The analysis was conducted with HPLC column (AsahiPak NH2P-50 4E, 4.6×250 mm) in a gradient condition for 130 minutes using 0.5 mM ammonium acetate (pH 6.7) and 250 mM ammonium acetate (pH 5.6) as mobile phases A and B, respectively. A fluorometric detector was used for detection, and the sum of the area of the peaks per number of sialic acids present at the terminal of N-glycan was calculated. In a case where there was no sialic acid, it was marked as neutral. In cases of one (monosialyl) and two (disialyl), they were marked as −1 and −2, respectively.

Experimental Example 1. Culturing Cell Strain Using Culture Medium not Comprising Insulin Added During Production Phase The same culture medium as that of the production phase in Example 2, excluding insulin, was used to culture the cell strain. N-Glycan contents (%) and relative surface area ratios (%) of O-glycopeptide per temperature were analyzed and are shown in Table 1 below.

TABLE 1

| Culture temperature (production phase) | Harvest ($N^{th}$) | N-Glycan-2 charge (%, avg) | Relative surface area ratio of O-glycopeptide (%, avg) |
|---|---|---|---|
| 30° C. | H1 | 12.5 | 56.13 |
| | H2 | | |
| | H3 | | |
| | H4 | | |
| 32° C. | H1 | 16.1 | 54.38 |
| | H2 | | |
| | H3 | | |
| | H4 | | |

Experimental Example 2. Comparison of Changes in Glycosylation Patterns According to Insulin Addition During the Production Phase The glycosylation patterns were compared in accordance with the insulin addition and are shown in Table 2 below.

TABLE 2

| Culture temperature | Insulin concentration in culture medium | Harvest ($N^{th}$) | N-Glycan-2 charge (%, avg) | Relative surface area ratio of O-glycopeptide (%, avg) |
|---|---|---|---|---|
| 30° C. | 0 mg/L | H1 | 12.5 | 56.13 |
| | | H2 | | |
| | | H3 | | |
| | | H4 | | |
| | 0.003 mg/L | H1 | 10.4 | 54.68 |
| | | H2 | | |
| | | H3 | | |
| | | H4 | | |
| | 0.009 mg/L | H1 | 10.9 | 52.68 |
| | | H2 | | |
| | | H3 | | |
| | | H4 | | |
| | 0.03 mg/L | H1 | 9.7 | 49.5 |
| | | H2 | | |
| | | H3 | | |
| | | H4 | | |

As a result, it was shown that among culturing processes of a cell capable of producing glycoprotein, the insulin addition during the production phase affected the glycosylation pattern. In particular, the N-glycan and/or O-glycan content was shown to change in accordance with the insulin addition. Specifically, it was confirmed that the N-glycan and/or O-glycan content could be controlled to be reduced by the insulin addition.

While the present invention has been described with reference to the particular illustrative embodiments, it will be understood by those skilled in the art to which the present invention pertains that the present invention may be embodied in other specific forms without departing from the technical spirit or essential characteristics of the present invention. Therefore, the embodiments described above are considered to be illustrative in all respects and not restrictive. Furthermore, the scope of the present invention is defined by the appended claims rather than the detailed description, and it should be understood that all modifications or variations derived from the meanings and scope of the present invention and equivalents thereof are included in the scope of the appended claims.

INDUSTRIAL APPLICABILITY

As it is capable of changing the N-glycan and/or O-glycan content according to the insulin addition particularly during the growth phase, the method of controlling glycosylation pattern of the recombinant glycoprotein according to the present invention can be very useful in production of a pharmaceutical recombinant glycoprotein in which uniformity of binding of saccharide molecules plays an important role.

The invention claimed is:

1. A method for controlling a glycosylation pattern of a recombinant glycoprotein, comprising culturing a microorganism comprising a polynucleotide encoding the recombinant glycoprotein in a culture medium comprising insulin, wherein said insulin is in an amount sufficient to reduce any N-glycans and/or O-glycans on said recombinant glycoprotein.

2. The method of claim 1, wherein the recombinant glycoprotein is an immunoglobulin fusion protein.

3. The method of claim 1, wherein the recombinant glycoprotein is a Tumor Necrosis Factor Receptor (TNFR)-Fc fusion protein.

4. The method of claim 1, wherein a concentration of the insulin is 0.0001 mg/L to 1 g/L relative to the total volume of the culture medium.

5. The method of claim 1, wherein the insulin controls N-linked glycosylation and O-linked glycosylation.

6. The method of claim 1, wherein the insulin reduces any N-glycan content of the recombinant glycoprotein.

7. The method of claim 1, wherein the insulin reduces any O-glycan content of the recombinant glycoprotein.

8. The method of claim 1, wherein the culturing is a perfusion culturing method.

9. A method for controlling a glycosylation pattern of a recombinant glycoprotein, comprising:
   (a) culturing a microorganism comprising a polynucleotide encoding a recombinant glycoprotein in a culture medium to grow the microorganism; and
   (b) adding insulin to the culture medium and culturing the same to produce a glycoprotein, wherein said insulin is added in an amount sufficient to reduce any N-glycans and/or O-glycans on said recombinant glycoprotein.

10. The method of claim 9, wherein said insulin is added at different concentrations to produce a target glycosylation pattern.

11. The method of claim 10, wherein the insulin is added in an amount sufficient to reduce the amount of any N-glycan or O-glycan on the recombinant glycoprotein.

12. The method of claim 9, wherein the recombinant glycoprotein is an immunoglobulin fusion protein.

13. The method of claim 9, wherein the recombinant glycoprotein is a TNFR-Fc fusion protein.

14. The method of claim 9, wherein a concentration of the insulin is 0.0001 mg/L to 1 g/L relative to the total volume of the culture medium.

15. The method of claim 9, wherein the culturing is a perfusion culturing method.

* * * * *